United States Patent [19]

Veltman

[11] Patent Number: 4,889,725

[45] Date of Patent: Dec. 26, 1989

[54] MEANS TO PROMOTE THE NEUTRALIZATION REACTION BETWEEN PARTICULATE CALCIUM CARBONATE AND IONIZED PHOSPHATE

[76] Inventor: Preston L. Veltman, 212 Old Country Rd., Severna Park, Md. 22146

[21] Appl. No.: 39,335

[22] Filed: Apr. 17, 1987

[51] Int. Cl.⁴ .......................................... A01N 59/10
[52] U.S. Cl. .................................... 424/675; 210/753; 423/308; 423/309; 423/431; 423/490; 424/687
[58] Field of Search ............... 423/490, 308, 431, 309; 424/52, 151, 156, 675, 687

[56] References Cited

U.S. PATENT DOCUMENTS

| | | | |
|---|---|---|---|
| 2,449,184 | 9/1948 | Strean | 424/52 |
| 2,671,755 | 3/1954 | Anderson | 424/151 |
| 3,179,493 | 4/1965 | Diekmann et al. | 423/431 |
| 3,227,617 | 1/1966 | Manahan et al. | 424/52 |
| 3,306,824 | 2/1967 | Laasko et al. | 424/151 |
| 3,655,867 | 4/1972 | Schoerning | 424/52 |
| 4,177,158 | 12/1979 | Blue | 423/244 A |
| 4,181,718 | 1/1980 | Mason et al. | 424/180 |
| 4,283,385 | 8/1981 | Dhabhar et al. | 424/52 |
| 4,472,368 | 9/1984 | O'Neill et al. | 423/490 |
| 4,578,376 | 3/1986 | Rosini | 514/108 |
| 4,629,130 | 12/1986 | Veltman | 241/16 |

OTHER PUBLICATIONS

P. Moriniere et al., Comparison of 1α-OH-Vitamin $D_3$ and High Doses of Calcium Carbonate for the Control of Hyperparathyroidism and Hyperaluminemia in Patients on Maintenance Dialysis, Nephron, 39:309-315, (1985).

Harvard Medical School Health Letter, Ulcer Drugs-Old and New, March 1986, vo. 11, No. 5.

E. Slatopolsky et al., Calcium Carbonate as a Phosphate Binder in Patient With Chronic Renal Failure Undergoing Dialysis, New England J. Med., vol. 315, No. 3, (1986).

Primary Examiner—John Doll
Assistant Examiner—Wayne A. Lange
Attorney, Agent, or Firm—Armstrong, Nikaido, Marmelstein, Kubovick & Murray

[57] ABSTRACT

A means for promoting the neutralization reaction between particulate calcium carbonate and ionized phosphate by adding a material formed by the reaction of particulate calcium carbonate and dilute hydrofluoric acid. The products of this invention are useful in lowering serum phosphate levels in patients undergoing renal dialysis, and are also useful as antacids. These products are also useful in the treatment of water and waste water to lower phosphate content.

5 Claims, 2 Drawing Sheets

MEANS TO PROMOTE THE NEUTRALIZATION REACTION BETWEEN PARTICULATE CALCIUM CARBONATE AND IONIZED PHOSPHATE

BACKGROUND OF THE INVENTION

1. Technical Field

This invention relates to a means for promoting the neutralization reaction between particulate calcium carbonate-derived products and ionized phosphate and to a process for the preparation of a modified calcium carbonate reactant.

2. Background Art

Calcium carbonate, in the form of limestone or in the form of pulverized shells from crustaceans, is a basic material used for the neutralization of acids. Calcium carbonate is a generally non-toxic material and the residues from its use provide no particular hazards for disposal.

In the medical fields, excessive acids present in the stomach and small intestine have been identified as a cause for pain and may be directly involved in either the formation of ulcers or the irritation thereof. Commercially available antacids typically contain calcium carbonate, magnesium hydroxide, aluminum hydroxide and combinations thereof. Unavoidable side effects from the use of these compounds include effects on bowel movements from magnesium hydroxide and aluminum hydroxide, magnesium tending to cause diarrhea and aluminum hydroxide causing constipation. Calcium compounds have the unfortunate side effect that a feedback mechanism results in the delayed generation of increased amounts of stomach acids. Sodium compounds, which are also available as antacids, are generally not preferred because the increased amount of sodium is contraindicated for persons on restricted diets to control hypertension and heart or kidney diseases. As a general rule, commercial antacids contain only trace amounts of sodium.

Serum phosphate levels serve an important regulatory function in mammals. Hyperphosphatemia is associated with the development of secondary hyperparathyroidism and renal osteodystrophy in patents with uremia. While the exact control mechanism is not clear, hyperphosphatemia appears to be related to calcium malabsorption which is commonly observed in patients with advanced renal insufficiency. Since serum calcium levels control the release of parathyroid hormone, if hyperphosphatemia can be avoided secondary hyperparathyroidism can be prevented (See Slatopolsky et al., *N. Engl. J. Med.*, 315, 157 (1986).

One mode of treatment for patients with hyperphosphatemia is the use of phosphate binders that contain aluminum. While this mode of treatment is generally successful in the short term, the accumulation of aluminum over an extended period of time results in the development of osteomalacia. Slatopolsky et al have shown that calcium carbonate, in particular Os-Cal ®, a commercially available calcium supplement which is derived from oyster shells, can be effective in the control of hyperphosphateima.

The use of a calcium carbonate compound as a phosphate binder, in place of aluminum containing compounds, offers obvious advantages but its utility is limited by the recognized hazard that metastatic calcification will occur in patients undergoing long term therapy. It is advisable, therefore, to limit the amount of calcium provided in a calcium carbonate-based phosphate binder.

A major commercial use for calcium carbonate is the treatment of acidic waters and gases for environmental protection. Granulated or pulverized limestone is typically the calcium carbonate source and numerous processes have been disclosed in the prior art to enhance the effectiveness of calcium carbonate for this purpose (see U.S. Pat. No. 4,629,130).

A particular concern, from an environmental standpoint, is the presence of phosphate in lakes and rivers. Excess phosphate causes algae blooms, which result in oxygen depletion of the water and the death of other organisms present. For this reason, the phosphate discharges should be controlled wherever possible but control is, at best, difficult. Conventional sewage treatment processes remove relatively small percentages of the phosphate entering the system and run-off from agricultural lands is rarely subject to any treatment.

It is known that the rate and extent of reaction between a given quantity of phosphate ion and a given quantity of particulate calcium carbonate is dependent on the physical capability of each phosphate ion to contact a calcium carbonate molecule in solution or at a surface. The efficiency of the reaction between phosphate ion and particulate calcium carbonate is impeded by the formation of the relatively insoluble tricalcium phosphate on the external surfaces of the calcium carbonate particle involved. As a result, when calcium carbonate is used to remove phosphate ions, an excess of calcium carbonate is typically required. In medical applications, the presence of excess calcium is undesirable. For non-medical uses the inefficiency of the reaction results in increased costs for treatment.

It is one object of this invention to provide a modified product comprising calcium carbonate having a more efficient neutralization reactivity towards phosphate ion when compared to the unmodified calcium carbonate conventionally used. It is a further object of this invention to provide a calcium carbonate comprising product for medical purposes having a significantly greater capacity, on a weight basis, for neutralizing phosphate ion in the presence of chloride ion as compared to the calcium carbonate used to prepare the product. A further objective is to provide a calcium carbonate comprising product suitable for inclusion in antacid preparations for the control of excess acid in the intestinal tract. A further objective is to provide a calcium carbonate comprising composition useful, when administered per os to lower blood serum phosphate levels and which also may be used to control serum calcium levels.

A further objective of this invention is to provide calcium carbonate and calcium fluoride containing compositions, having solubility characteristics suitable for ingestion, to supply fluoride ion and calcium ion for therapeutic purposes. A still further object is to provide calcium carbonate containing products having added fluoride suitable, when used in admixture with Vitamin D and other adjuvants to be utilized in the manufacture of calcium carbonate containing therapeutic agents. (A commercially available calcium carbonate product containing calcium and Vitamin D in the ratio of 250 mg Ca to 125 USP units of Vitamin D is Os-Cal ®, manufactured by Marion Laboratories, Kansas City, Mo. 64137). A further objective of this invention is to provide a fluoride ion containing mild abrasive suitable for use in dentifrices.

It is a further objective of this invention to provide an improved method for the removal of phosphate ion from rivers, lakes and streams, and in industrial process, by providing a calcium carbonate containing product having a more efficient neutralization reactivity toward phosphate ion and having a significantly greater capacity, on a weight basis for neutralizing phosphate ion. A further objective is to provide enhanced reactivity in the presence of ubiquitous environmental contaminants such as chloride ion.

SUMMARY OF THE INVENTION

This invention provides means to promote the neutralization reaction between particulate calcium carbonate and ionized phosphate. Calcium carbonate containing minor amounts of molecularly dispersed calcium fluoride, prepared by dispersing particulate calcium carbonate in dilute aqueous hydrofluoric acid can be employed to removed phosphate ions at a higher efficiency than untreated particulate calcium carbonate. The treated calcium carbonate particles containing calcium fluoride are effective in the removal of phosphate ions in the presence of chloride ions, such as would be encountered in gastric juices. The preferred amount of fluoride present is 2 to 5% as $CaF_2$ by weight.

Calcium carbonate containing molecularly dispersed calcium fluoride can be prepared using calcium carbonate derived from oyster shell or limestone and the products of this invention ma be used for the treatment of hyperphosphatemia, gastric ulcers and other diseases wherein the control of acidity and serum phosphate are required.

Particulate calcium carbonate containing molecularly dispersed calcium fluoride may be used to remove phosphate from industrial and household effluents and in the treatment of rivers, lakes and streams containing excess phosphate levels.

DETAILED DESCRIPTION OF THE INVENTION

Figure 1:
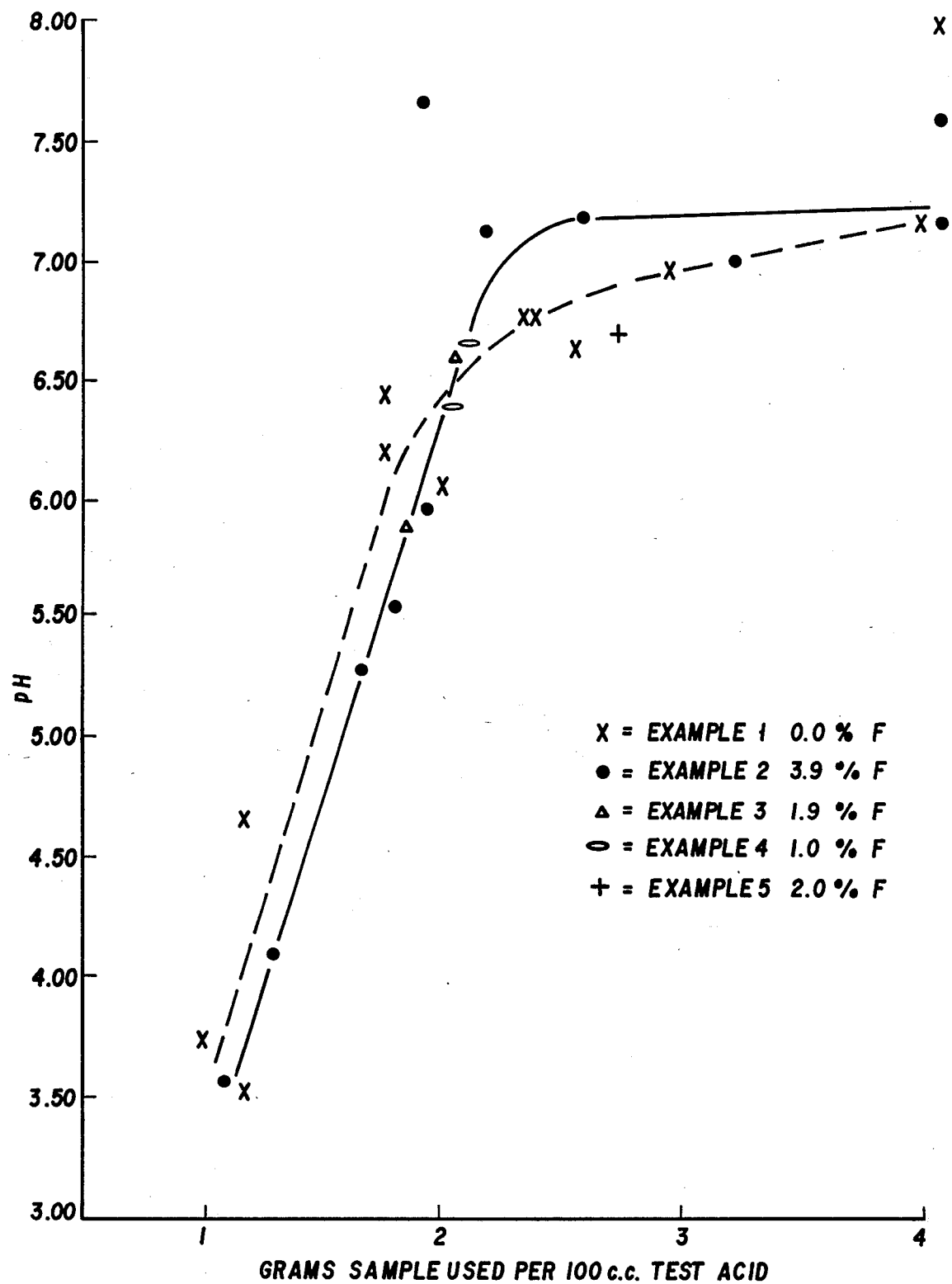
FIG. 1 is a plot of pH versus grams of sample required to achieve neutralization of a given quantity of acids using calcium carbonate materials containing different levels of fluoride.

Phosphate ions in molecular contact with particulate calcium carbonate react to form mono-,di-,and tri-calcium phosphates. Calcium phosphate salts vary greatly in water solubility, ranging from 2 to $3 \times 10^{-3}$ g per 100 ml for tri-calcium phosphate to 1.8 grams per 100 ml for the mono-calcium phosphate. The rate and extent of reaction between any given quantity of phosphate ion and any given quantity of particulate calcium carbonate is dependent upon the physical capability of each phosphate ion to contact a calcium carbonate molecule in solution or at a surface. Calcium carbonate has a solubility of only $1.5 \times 10^{-3}$ g per 100 ml and the efficiency of the reaction between phosphate ions and particulate calcium carbonate is further impeded by the formation of the relatively insoluble tri-calcium phosphate on the external surfaces of the calcium carbonate particles.

This invention is based upon the discovery that the efficiency of the reaction between calcium carbonate and phosphate ion may be promoted by supplying a quantity of fluoride to the system. More specifically, this invention resides in the provision of molecularly dispersed fluoride in a particulate calcium carbonate by dispersing finely ground calcium carbonate in a dilute aqueous solution of hydrofluoric acid. After removal of the water, such as by evaporation, the treated calcium carbonate may be used as a powder, formed into pills, packed into capsules or dispersed in a liquid or gel for use in that manner.

A preferred source of calcium carbonate is obtainable from oyster shells and is available in pharmaceutical grades as oyster shell flour. This is the active calcium source in products such as Os-Cal ®. An alternative source of calcium carbonate is finely ground limestone rock.

While not wishing to be bound by any theoretical explanation of this invention, it is believed that the reaction between a calcium carbonate product prepared in accordance with this invention and phosphate ions when compared with untreated calcium carbonate resides in the molecular species which is ultimately formed. It is known that phosphate in natural phosphate minerals is essentially unavailable for utilization by plants and animals and, in commercial practice, phosphate rock and bone phosphate sources must be first treated by chemical or thermal means to remove fluoride. Natural phosphate minerals are predominately fluorapatite, a mineral comprising calcium, phosphorous, oxygen and fluorine and having an empirical formula of $Ca_3(PO_4)_2.CaF_2$. The solubility of fluorapatite in water is essentially zero. A related compound, hydroxyapatite, partly carbonated, makes up the mineral parts of teeth.

When a quantity of fluoride between 2 and 5%, as $CaF_2$, is present in the treated calcium carbonate as taught in this invention, it is possible to create, upon reaction with phosphate ion, a molecular species approximating the natural fluorapatite composition. The insoluble precipitate effectively removes phosphate from the system.

Treatment of calcium carbonate with dilute HF apparently results in the formation of a different crystalline structure in the calcium carbonate and avoids the coating phenomenon wherein tri-calcium phosphate apparently is formed on the external surfaces of particulate calcium carbonate, which presumably prevents the obtainment, in practice, of the formation of calcium phosphate using the theoretical equivalent amount of calcium carbonate. Since fluorapatite is less soluble than calcium phosphates, there is no phosphate ion in the solution at equilibrium and essentially theoretical amounts of the treated calcium carbonate material can be employed.

When the calcium carbonate treated by the addition of molecularly dispersed fluoride is used as a pharmaceutical composition to lower serum phosphate levels, the amount of calcium which must be administered to achieve the desired reduction in serum phosphate levels may be lower than the amount which would be required in the absence of treatment. For example, Slatopolsky et al. report that 8.5 grams of Os-Cal ® was required to obtain a decrease in serum phosphate equivalent to that obtained with aluminum containing compounds in test subjects. According to this invention, this value can, theoretically be reduced to 6.0 grams per day and could provide a means for reducing potential side effects such as metastatic calcification.

If the treated calcium carbonate containing compositions of this invention were administered orally, they would first interact with saliva, which has a pH of approximately 6.7. Upon entering the stomach, the materials administered would encounter solutions of hydrochloric acid approximating 0.03 N although higher acid concentrations may be encountered locally as a result of stimulation of the gastric glands. It is essential, therefore, that phosphate precipitating compounds must be effective in the presence of chloride ion. Since calcium carbonate reacts with hydrochloric acid to form, ultimately, carbon dioxide, water, and dissolved calcium chloride the compounds of this invention would still be capable of providing the calcium and fluoride necessary to be effective for the removal of phosphate ions even in the presence of excessive stomach acid levels.

Administration of the compounds of this invention, therefore, would provide an effective means for lowering serum levels of phosphate without introducing any irritants into the stomach and gastric tract. The insoluble precipitate which is formed is non-toxic and readily discharged through the bowels, thereby removing both the phosphate and excess calcium. The compounds of this invention also are a mild abrasive suitable for use in a dentifrice and do not require the addition of another source of fluoride for the control of dental caries.

When used for the removal of phosphate from industrial and household effluents, the water-insoluble precipitates could be easily removed by settling, filtration, or some combination thereof. Since the precipitate is equivalent in composition to naturally occurring minerals, disposal on land creates no significant environmental hazard and, indeed, the material may be recycled as a source of phosphate.

In the treatment of lakes containing excessive amounts of phosphate, the compounds of this invention may be added directly and the phosphate effectively precipitated in a form which is non toxic to fish, crustaceans and normal lake flora.

The above and other objects and the attendant advantages of the present invention will become readily apparent by reference to the following detailed description, when considered in conjunction with the accompanying Tables and Figures.

EXPERIMENTAL PROTOCOL

It is known that the relative phosphate ion neutralization utility of various products can be established by determining the weight of each calcium carbonate comprising material required to neutralize a given quantity of acid. Hydrochloric and phosphoric acids are the primary acids of concern. Their concentration determines the pH of gut contents and the serum phosphate ion concentration in the blood. In the following experiments, the quantity of total acid used in each test was kept constant, while the amount of each neutralizing sample was varied. The pH obtained at equilibrium was noted and used as a measure of the neutralization efficiency and phosphate binding capacity.

A standard acid concentrate containing 0.33 mol of HCl (12.15 grams) and 0.67 mol of $H_3PO_4$ (65.33 grams) was admixed with water to a volume of one liter. A 100 ml aliquot of diluted acid containing 14.42 ml of the acid concentrate was prepared for each experiment.

EXAMPLE 1

Five hundred grams of oyster flour obtained from Oyster Shell Products, P.0. Box 1225, Mobile, Ala., and representative of the materials used in the preparation of antacid medicinal products, was dispersed in 1000 grams of deionized water. The aqueous phase had a pH of 9.65 after three days standing. The water content was then removed by evaporation at 100° C. to constant weight. By analysis, the dried material contained 85.25% calcium carbonate. The material was readily friable and screened through a 60-mesh screen to form Sample 1.

EXAMPLE 2

Five hundred grams of oyster shell flour, as used in Example 1, was rapidly dispersed in one liter of an aqueous solution containing 20 grams of HF. After three days standing, the pH of the aqueous dispersion was found to be 6.53. The water was then removed by heating at 100° C. to constant weight and screened through a 60-mesh screen. The product was found to contain 7.97% calcium fluoride (3.9% F), 76.94% calcium carbonate and 15.08 chetin and other naturally occurring materials naturally occurring in oyster shell products and is identified as Sample 2.

EXAMPLE 3

Five hundred grams of oyster shell flour, as used in the preparation of Example 1, was rapidly dispersed in one liter of a solution containing 10 grams of HF. After three days standing, the aqueous dispersion was found to have a pH of 6.7. The water was removed by evaporation at 100° C. to constant weight and the dried material passed through a 60-mesh screen. The product contained 4% calcium fluoride (1.9% F), 81% calcium carbonate and 15% chetin and other naturally occurring materials, and was identified as Sample 3.

EXAMPLE 4

Five hundred grams of oyster shell flour, as used in Example 1, was rapidly dispersed in one liter of a solution containing 5 grams of HF. After three days standing the pH of the aqueous phase was found to be 7.1. The water was removed by evaporation at 100° C. to constant weight and the dried material was passed through a 60-mesh screen. The sample was found to contain 2% calcium fluoride (1% F), 84% calcium carbonate and 14% chetin and other materials, and identified as Sample 4.

EXAMPLE 5

A portion (480 grams) of the product of Example 1 was physically mixed with 20 grams of chemically pure calcium fluoride to produce Sample 5, having a calcium fluoride content of 4% (2% F).

EXAMPLE 6

Chemically pure, precipitated, calcium carbonate (425 grams) was dispersed with mixing in a water solution containing 20 grams of HF. After three days standing, the water was removed by drying at 100° C. to constant weight and the product screened through a 60-mesh screen. The product contained 9.4% $CaF_2$ (4.8% F), and 90.6% $CaCO_3$ and identified as Sample 6.

EXAMPLE 7

Five hundred grams of pigment grade limestone, having a mean particle diameter of less than six micrometers, and a calcium carbonate content of 90%, was dispersed with efficient mixing in a solution containing 20 grams of HF. After three days standing, the material was dried to constant weight at 100° C. and found to contain 8% CaF₂ (4% F) and 82% CaCO₃, and was identified as Sample 7.

EXAMPLE 8

Aliquots of dried Samples 1–7 were placed in jars equipped with a screw lid fitted with a foam polystyrene liner and 100 ml of the test acid, as described above, containing 0.1752 grams of HCl and 0.9420 grams of $H_3PO_4$ was added. The contents were hand stirred for one minute and evolution of carbon dioxide was observed. The lid was then placed on the jar and the contents allowed to stand at room temperature of approximately 70% F for 24 hours. Periodically, the jars were shaken to assure thorough mixing.

After 24 hours, the contents of each jar was placed in a 250 ml flask containing a magnetic stir bar and fitted with a thermometer. The flask, including contents, was weighed and the weight noted to the nearest one-one hundredth of a gram. After weighing, the flask and contents were placed on a hot plate equipped with a magnetic stirrer and the contents heated to a temperature of between 80° and 90° C. and maintained at that temperature for approximately 3 minutes. During this period, residual carbon dioxide was evolved and approximately 1 gram of water lost.

After cooling, the flask contents were weighted and deionized water added to replace that lost during heating. The solution was then filtered using Whatman No. 4 qualitative filter paper and the solution placed in a jar fitted with a screw top and allowed to cool to room temperature. The pH of the solution was determined to the nearest one-one hundredth of a pH unit using a digital pH meter (Orion Research Model 601A).

The conductivity of each solution was measured to the nearest one-hundredth mS/Cm with a calibrated conductivity meter (Extech Instruments, Model 690, available from Extech Instruments, 150 Bearhill Road, Waltham, Mass., calibrated using dilute KCl solutions). The results are shown in Table 1 and plotted in FIG. 1.

TABLE 1

|  | Grams Sample Used Per 100 ml Test Acid | Grams CaCO₃ in Sample | pH at Equi-librium | Conductivity m S/Cm |
|---|---|---|---|---|
| Example 1 | 1.00 | 0.85 | 3.75 | 8.27 |
| 0.0% F. | 2.00 | 1.71 | 6.06 | 5.21 |
| in Samples | 4.00 | 3.41 | 7.16 | 5.21 |
|  | 7.00 | 5.91 | 7.18 | 5.06 |
|  | 1.76 | 1.50 | 6.20 | 6.65 |
|  | 1.17 | 1.00 | 3.52 | 8.46 |
|  | 2.35 | 2.00 | 6.78 | 6.54 |
|  | 2.58 | 2.20 | 6.63 | 6.45 |
|  | 1.17 | 1.00 | 4.67 | 8.12 |
|  | 1.76 | 1.50 | 6.45 | 6.75 |
|  | 2.35 | 2.00 | 6.78 | 6.55 |
|  | 2.93 | 2.50 | 6.98 | 6.61 |
|  | 4.10 | 3.50 | 7.98 | 6.79 |
| Example 2 | 1.95 | 1.50 | 7.65 | 6.70 |
| 3.9% F. | 1.82 | 1.40 | 5.54 | 6.46 |
| in samples | 1.69 | 1.30 | 5.28 | 6.50 |
|  | 1.30 | 1.00 | 4.09 | 8.33 |
|  | 1.95 | 1.50 | 5.98 | 6.72 |
|  | 2.60 | 2.00 | 7.19 | 6.54 |
|  | 3.25 | 2.50 | 7.00 | 6.58 |
|  | 4.56 | 3.50 | 7.50 | 6.70 |
|  | 1.10 | 0.85 | 3.58 | 7.92 |
|  | 2.20 | 1.71 | 7.11 | 5.12 |
|  | 4.40 | 3.41 | 7.09 | 5.18 |
|  | 7.70 | 5.97 | 7.44 | 5.04 |
| Example 3 | 1.85 | 1.50 | 5.90 | 6.70 |
| 1.9% F. | 2.04 | 1.65 | 6.60 | 6.55 |

TABLE 1-continued

|  | Grams Sample Used Per 100 ml Test Acid | Grams CaCO₃ in Sample | pH at Equi-librium | Conductivity m S/Cm |
|---|---|---|---|---|
| in Samples Example 4 | 2.02 | 1.70 | 6.40 | 6.75 |
| 1.0% F. in Samples | 2.14 | 1.80 | 6.65 | 6.55 |
| Example 5 2% F. in Sample | 2.74 | 2.25 | 6.70 | 6.65 |
| Example 6 4.8% F. in Sample | 2.10 | 1.90 | 7.05 | 6.57 |
| Example 7 4% F. in Sample | 2.30 | 1.89 | 7.12 | 5.12 | contained in 100 ml of an acid solution containing 0.1752 grams of HCl and 0.9420 grams of $H_3PO_4$. Sample 2, containing 3.9% F, required 2.25 grams to neutralize 100 ml of the acid test solution. Thus, for a given amount of hydrochloric and phosphoric acid containing solution, only 70% of the weight of material containing 3.9% F is required to neutralize the same amount of acid as can be neutralized using untreated calcium carbonate.

The effect of decreasing the amount of F present in the treated calcium carbonate is shown in the results for Samples 3 and 4.

The presence of calcium fluoride as individual particles but not molecularly dispersed is shown in the data for Sample 5. Comparison of the results for Samples 2, 3, 4 and 5 shows that the presence of calcium fluoride as individual particles has no significant effect on the neutralization reaction, whereas the presence of the molecularly dispersed calcium fluoride lessens the amount of material needed to achieve neutralization.

The data for Samples 6 and 7 indicate that both pure, precipitated calcium carbonate and pigment grade limestone are suitable for use in preparing products of this invention.

Figure 2:
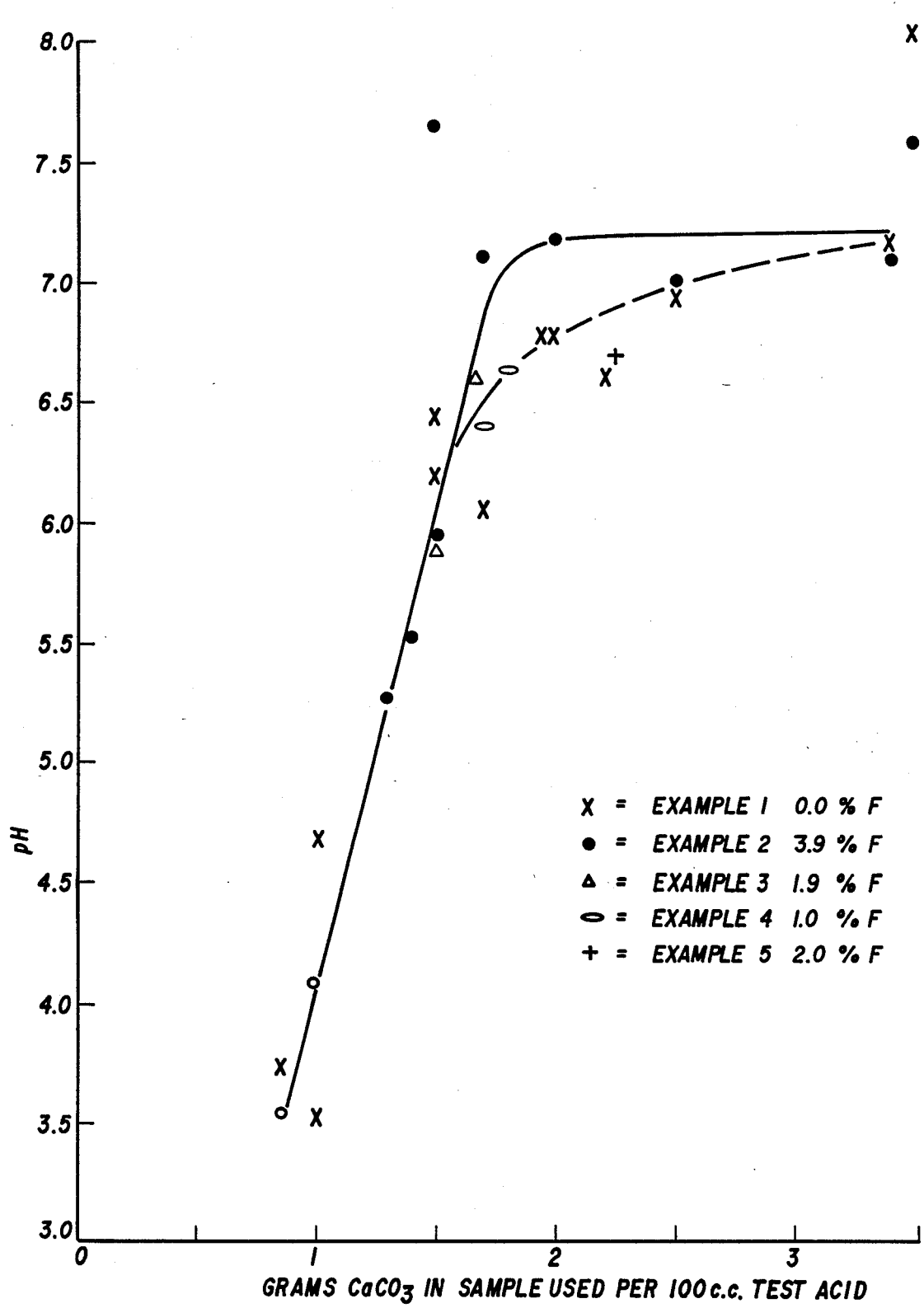
FIG. 2 is a plot of pH versus grams of calcium carbonate required to achieve neutralization of a given quantity of acids.

FIG. 2 shows data plotted relating the calcium carbonate content of the materials tested for neutralization capacity. Sample 1 require 2.5 grams to neutralized 100 ml of test acid, whereas only 1.75 grams of Sample 2 were required.

Conductivity measurements show the total concentration of ions present in the solution. As shown in Table 1, a marked decrease in conductivity occurs near a pH of 7, indicating that precipitation has occurred. The principle source of ions at a pH of 7 is believed to be derived from calcium chloride formed during neutralization.

The results reported above clearly show the untreated calcium carbonate, which does not contain fluoride (Sample 1) does not react quantitatively to precipitate phosphate. Calcium carbonate particulates react rapidly and completely with hydrochloric acid producing soluble calcium chloride and gaseous carbon dioxide. Calcium carbonate particles do not react rapidly with phosphoric acid, due to the apparent formation of the relative insoluble calcium phosphates on the surface of the particles. Assuming that all of the hydrochloric acid in the test acid reacted with calcium carbonate to form calcium chloride and carbonic acid and that all of the phosphoric acid reacted to form calcium phosphate and carbonic acid and further assuming that the calcium fluoride present would associate with calcium phosphate to produce the insoluble fluorapatite, the resulting product should have the following approximate mol ratios of components:

| | |
|---|---|
| 1 mol | $Ca_3(PO_4)_2 \cdot CaF_2$ |
| 1.1 mol | $Ca_3(PO_4)_2$ |
| 0.82 mol | $CaCl_2$ |

The quantitative superiority, insofar as the relative weight of material required to neutralize given amounts of acids, is therefore believed due, at least in part, to the in situ formation of highly insoluble fluorapatite.

EXAMPLE 9

A dental paste may be prepared according to the following formulation:

| | |
|---|---|
| Composition of Example 2 | 45 parts |
| Sorbitol | 15 parts |
| Glycerine | 15 parts |
| Sodium carboxymethylcellulose | 1 part |
| Saccharin | 0.5 parts |
| Titanium dioxide | 0.5 parts |
| Water | balance |

It is readily apparent that the above described calcium carbonate comprising product containing molecularly dispersed fluoride meets all of the objects mentioned above and also has the advantage of wide commercial utility. It should be understood that the specific form of the invention hereinafter described is intended to be representative only, as certain modifications within the scope of these teachings will be apparent to those skilled in the art.

Accordingly, reference should be made to the following claims in determining the full scope of the invention.

I claim:

1. A pharmaceutical composition consisting essentially of calcium carbonate containing a minor amount of molecularly dispersed calcium fluoride, formed by the process of dispersing particulate calcium carbonate in a dilute aqueous solution of hydrofluoric acid and drying the treated product.

2. A pharmaceutical composition according to claim 1 which is a powder.

3. A pharmaceutical composition according to claim 1 further comprising Vitamin D.

4. A pharmaceutical composition according to claim 1, wherein said dilute aqueous solution of hydrofluoric acid contains 1 to 10% by weight HF, based upon the weight of calcium carbonate.

5. A pharmaceutical composition comprising:
   a hyperphosphatemia lowering amount of a composition consisting essentially of calcium carbonate containing a minor amount of molecularly dispersed calcium fluoride, formed by the process of dispersing particulate calcium carbonate in a dilute aqueous solution of hydrofluoric acid; and
   a pharmaceutically acceptable carrier.

* * * * *